(12) United States Patent
Pisegna

(10) Patent No.: US 7,365,047 B1
(45) Date of Patent: Apr. 29, 2008

(54) USE OF PENTAGASTRIN TO INHIBIT GASTRIC ACID SECRETION OR AS A DIURETIC

(75) Inventor: Joseph R. Pisegna, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 302 days.

(21) Appl. No.: 09/671,764

(22) Filed: Sep. 27, 2000

Related U.S. Application Data

(60) Provisional application No. 60/156,491, filed on Sep. 28, 1999.

(51) Int. Cl.
*A61K 38/00* (2006.01)
*A61K 49/00* (2006.01)

(52) U.S. Cl. .............................. 514/2; 514/13; 514/17; 514/199; 514/256; 514/338; 514/361; 530/300; 530/326; 530/330; 424/9.1

(58) Field of Classification Search ................ 514/2, 514/13, 17, 361, 256, 338, 199; 530/300, 530/326, 330; 424/9.1
See application file for complete search history.

(56) References Cited

U.S. PATENT DOCUMENTS

| | | | |
|---|---|---|---|
| 4,997,950 A * | 3/1991 | Murphy et al. ............. | 548/303 |
| 5,629,305 A | 5/1997 | Eek et al. | |
| 5,750,531 A | 5/1998 | Lee et al. | |
| 5,877,192 A | 3/1999 | Lindberg et al. | |
| 6,013,281 A | 1/2000 | Lundberg et al. | |
| 6,093,738 A | 7/2000 | Karimian et al. | |

OTHER PUBLICATIONS

PCT Search Report for International Application No. PCT/US00/26992.
Campoli-Richards et al. (1986) "Famotidine Pharmacodynamic and Pharmacokinetic Properties and a Preliminary Review of its Therapeutic Use in Peptic Ulcer Disease and Zollinger-Ellison Syndrome", Drugs 32: 197-221.
Chin et al. (1986) "Absence of Tachyphylaxis in Gastric Acid Secretion During Pentagastrin Infusion" J. Clin. Pharmacol. 26: 281-285.
Davidson et al. (1973) "Renal Extraction and Excretion of Endogenous Gastrin in the Dog", Gastroenterology 64: 955-961.
Desanto et al. (1992) "Brain-Gut Peptides and the Renal Hemodynamic Response to an Oral Protein Load: A Study of Gastrin, Bombesin, and Glucagon in Man", Renal Physiol. Biochem. 15: 53-56.
Deveney et al. (1983) "Cimetidine in the Treatment of Zollinger-Ellison Syndrome", Amer. J. Surg. 146: 116-123.
Drogden et al. (1978) "Cimetidine: A Review of its Pharmacological Properties and Therapeutic Efficacy in Peptic Ulcer Disease", Drugs 15: 93-131.
El Munshid et al. (1980) "Importance of the Kidneys for Gastrin Elimination and Gastric Function", J. Physiol. 299: 157-171.

Hansky (1979) "Effect of Renal Failure on Gastrointestinal Hormones", World J. Surg. 3: 463-467.
Hartman et al. (1998) "Equipotent Inhibition of Gastric Acid Secretion by Equal Doses of Oral or Intravenous Pantoprazole", Aliment. Pharmacol. Ther. 12: 1027-1032.
Hirschowitz et al. (1995) "Pharmacological Aspects of Acid Secretion", Dig. Dis. Sci. 40: 2 (suppl) 3S-23S.
Hostetter (1986) "Human Renal Response to a Meat Meal", Am J. Physiol 250: F613-F618.
Howard et al. (1985) "Famotidine, a New Potent, Long-Acting Histamine H2-Receptor Antagonist: Comparison With Cimetidine and Ranitidine in the Treatment of Zollinger-Ellison Syndrome", Gastroenterology 88: 1026-1033.
Kes et al. (1993) "Influence of Renal Functional Mass on the Catabolism of Endogenous Gastrin in Humans", Renal Physiol. Biochem. 16: 268-275.
Lotti and Chang (1989) "A New Potent and Selective Non-Peptide Gastrin Antagonist and Brain Cholectstokinin Receptor (CCK-B) Ligand: L-365,260", Eur. J. Pharmacol. 162: 273-280.
Mason et al. (1969) "Continuous Intravenous Pentagastrin as a Stimulant of Maximal Gastric Acid Secretion", Gut, 10: 34-38.
McCarthy (1978) "Report on the United States Experience with Cimetidine in Zollinger-Ellison Syndrome and Other Hypersecretory States", Gastroenterology 74: 453-458.
Nielsen et al. (1980) "The Effect of Renal Transplantation on Basal Serum Gastrin Concentration", Acta. Med. Scand. 207: 85-87.
Bonfils et al. (1979) "Cimetidine Treatment of Acute and Chronic Zollinger-Ellison Syndrome", World J. Surg. 3: 597-604.
Rume et al. (1981) "Abstracts of Papers", Gastroenterology 80:1265.
Saeed et al. (1989) "Parenteral Antisecretory Drug Therapy in Patients with Zollinger-Ellison Syndrome", Gastroenterology 96: 1393-1402.
Schjonsby and Willassen (1977) "Renal Extraction of Endogenous Gastrin in Patiens with Normal Renal Function", Gastroenterology 12: 205-207.
Simon et al. (1990) "Single Intravenous Administration of the H+, K+-ATPase Inhibitor BY 1023/SK&F 96022-Inhibition of Pentagastrin-Stimulated Gastrin Acid Secretion and Pharmacokinetics in Man", Aliment Pharmacol. Therap. 4: 239-245.
Simon et al. (1990) "Pentagastrin-Stimulated Gastric Acid Secretion and Pharmacokinetics Following Singe and Repeated Intravenous Administration of the Gastric H+, K+-ATPase-Inhibitor Pantoprazole (BY1023/SK&F96022) in Healthy Volunteers", Z. Gastroenterology 28: 443-447.
Vallot et al. (1983) "Evaluation of Antisecretory Drug Therapy of Zollinger-Ellison Syndrome (ZES) Using 24 Hour pH Monitoring", Dig. Dis. Sci. 28: 7: 577-584.

(Continued)

*Primary Examiner*—Chih-Min Kam
(74) *Attorney, Agent, or Firm*—Weaver Austin Villeneuve & Sampson LLP; Tom Hunter

(57) ABSTRACT

This invention pertains to the discovery that pentagastrin, when administered in conjunction with a proton pump inhibitor (PPI) is synergistic with the PPI and significantly increases the efficacy of the PPI in reducing/mitigating excess gastric acid secretion.

20 Claims, 6 Drawing Sheets

OTHER PUBLICATIONS

Wank et al. (1992) "Brain and Gastrointestinal Cholecystokinin Receptor Family: Structure and Functional Expression", Proc. Natl. Acad. Sci. USA 89: 8691-8695.

Wormsley et al. (1966) "Effects of a Gastrin-Like Pentapeptide (I.C.I. 50, 123) on Stomach and Pancreas", Lancet, 1: 993-996.

Fraker et al. (1988) "A Prospective Study of Perioperative and Postoperative Control of Acid Hypersecretion in Patients with Zollinger-Ellison Syndrome Undergoing Gastrinoma Resection", Surgery 104: 6: 1054-1063.

de Graef and Woussen-Cole (1986) "Influence of the Stimulation State of the Parietal Cells on the Inhibitory Effect of Omeprazole on Gastric Acid Secretion in Dogs", Gastroenterology 9;: 333-337.

Kromer et al. (2000) "Animal Pharmacology of Reversible Antagonism of the Gastric Acid Pump, Compared to Standard Antisecretory Principles" Pharmacology 60: 179-187.

Richardson et al. (1998) Proton Pump Inhibitors: Pharmacology and Rationale for use in Gastrointestinal Disorders Drugs 56 (3) 307-335.

* cited by examiner

USE OF PENTAGASTRIN TO INHIBIT GASTRIC ACID SECRETION OR AS A DIURETIC

CROSS-REFERENCE TO RELATED APPLICATIONS

This application claims priority to and benefit of U.S. Ser. No. 60/156,491, filed on Sep. 28, 1999 which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under a grant awarded by the Veterans Administration. The Government of the United States of America may have certain rights in this invention.

FIELD OF THE INVENTION

This invention relates to the treatment of physiological disorders characterized by excess gastric acid secretion. In particular, this invention relates to the use of pentagastrin as a synergist with proton pump inhibitors (PPIs).

BACKGROUND OF THE INVENTION

A wide number of pathological conditions are characterized by oversecretion of gastric acid. Such conditions include, but are not limited to, Zollinger/Ellison syndrome (ZES), gastroesophageal reflux disease, peptic ulcer disease, duodenal ulcers, atrophic gastritis, esophagitis, and the like. Conditions such as ZES and peptic ulcers, in particular, can have serious complications and represent some of the most prevalent diseases in industrialized nations.

The treatment of such conditions often requires high and repeated doses of acid output (AO) inhibiting agents to effectively reduce intragastric acidity. Although histamine $H_2$-antagonists have been used successfully to treat such conditions, the erratic and diminishing responses with these antagonists as well as the progressive occurrence of more sever side effects associated with the use of larger doses has led to the use of the more effective proton pump inhibitors (PPIs).

Proton pump inhibitors (PPI) are potent inhibitors of gastric acid secretion by inhibiting $H^+/K^+$-ATPase, the enzyme involved in the final step of hydrogen ion production in the parietal cells. Hence, PPI have been used in the treatment of gastric acid related diseases in humans. Despite their wide-spread use, means of increasing PPI efficacy, e.g. at a lower dose are desired.

SUMMARY OF THE INVENTION

This invention provides a novel method of treating pathological conditions characterized by excess gastric acid secretion. In particular, this invention pertains to the discovery that administration of pentagastrin (an agent that is typically used to increase acid secretion), in conjunction with a proton pump inhibitor (PPI) will result in increased efficacy (e.g. prolonged effect and/or greater effect at reduced dosage) than use of the proton pump inhibitor alone. The effect is also mediated by gastrin and gastrin or pentagastrin analogues or derivatives. In particular embodiments, the pentagastrin/PPI combination appears synergistic.

Thus, in one embodiment, this invention provides methods of increasing the efficacy of a gastric $H^+/K^+$-ATPase pump inhibitor (PPI) in a mammal (e.g. a rodent, largomorph, bovine, canine, equine, non-human primate, human, etc.). The methods preferably involve administering to the mammal pentagastrin, gastrin or analogues or derivatives thereof in conjunction with a gastric proton pump inhibitor. Pentagastrin is used in particularly preferred embodiments. The pentagastrin can be administered before, simultaneously with, or after the PPI, but in a most preferred embodiment, the pentagastrin administration precedes the PPI administration. In addition to the use of exogenous gastrin or pentagastrin, the method can involve upregulating endogenous gastrin secretion using, for example, aromatic amino acids, or with a meal, etc. Essentially anything that stimulates G-cell activity will increase the efficacy of a PPI.

Administration of the gastrin/pentagastrin/analogue and the PPI can be by any route convenient for the application of these agents. In preferred embodiments, the gastrin/pentagastrin/analogue is administered by injection (e.g. subcutaneous injection) and the PPI is administered orally or by injection (e.g. intravenous injection). Particularly preferred pentagastrin/gastrin/analogue dosages range from about 0.1 mg/kg/hr to about 10 mg/kg/hr.

The mammal is preferably a mammal diagnosed with a pathology characterized by excess gastric acid secretion, e.g., Zollinger/Ellison syndrome (ZES), gastroesophageal reflux disease (GERD), peptic ulcer disease, atrophic gastritis, esophagitis, stress induced hypersecretion, and/or idiopathic gastric acid hypersecretion. Preferred proton pump inhibitors used in this invention include, but are not limited to rabeprazole, omeprazole, lansoprazole, and pantoprazole, as well as cogeners or racemic mixtures of the same. The mammal may also suffer from hypersensivity to normal acid secretion that may result in gastrointestinal inflammation and ulceration.

This invention also involves the discovery that administration of pentagastrin gastrin or analogues thereof or other compounds that act at the same receptor site (e.g. that are agonistic at the cholecystokinin (CCK) receptor (see, U.S. Pat. No. 5,319,073 for a description of the CCK receptor) will increase urinary sodium excretion (e.g. gastrin, pentagastrin, cholecystokinin and derivatives or analogues thereof act as a diuretic). Thus, in another embodiment, this invention provides methods of increasing urinary sodium excretion and free water excretion. These methods involve administering to a mammal diagnosed with a pathological condition characterized by excessive fluid retention, a dose of pentagastrin or analogues thereof (or in certain embodiments, gastrin or analogues thereof) sufficient to increase urinary sodium excretion in the mammal. In preferred embodiments, the pathological condition is high blood pressure, fluid retention associated with heart failure, fluid retention associated with acute or chronic kidney failure, fluid retention associated with cirrhosis, calcium kidney stones, nephrogenic diabetes insipidus, renal tubular acidosis, treatment of Meniere's disease, constrictive pericarditis, and hepatorenal syndrome. The pentagastrin is typically administered in the dosage ranges indicated above.

Kits are also provided for the practice of the methods of this invention. A preferred kit for the treatment of a pathology characterized by excess gastric acid secretion, said kit comprises a container containing a proton pump inhibitor (PPI); and a container containing pentagastrin. Preferred proton pump inhibitors include, but are not limited to rabeprazole, omeprazole, lansoprazole, and pantoprazole, as well as cogeners or racemic mixtures of the same. The pentagastrin and/or the PPI can be provided in a pharmaceutically acceptable excipient or diluent. The kits can additionally include materials describing the use of pentagastrin, gastrin or analogues thereof in conjunction with a PPI to reduce gastric acid secretion and/or materials describing the use of pentagastrin as a diuretic. Instructional materials can also include recommended dosages and description(s) of counterindications, etc.

Also included are kits for increasing urinary sodium excretion in a mammal. Preferred kits comprise a container containing a pentagastrin, gastrin, or analogue thereof; and instructional materials describing the use of said pentagastrin, gastrin, or analogue thereof to increase urinary sodium excretion in a mammal.

DEFINITIONS

The "$H^+/K^+$-ATPase" or "proton pump" is an acid pump responsible for the final step of acid secretion (see, e.g., Besancon et al. (1996) *J. Biol. Chem.* 272: 22438-22446; Lambrecht et al. (1998) J. Biol. Chem. 273:13719-28; Nwokolo et al. (1991) Gut; 32:1455; Sachs et al.: (1995) *Ann Rev Pharm Toxic.* 35: 277-305. It is believed the "proton pump" is a heterodimer. The catalytic subunit has ten membrane-inserted segments and the beta subunit a single transmembrane segment. The proton pump typically catalyzes an electroneutral $H^+$ for $K^+$ exchange.

"Proton pump inhibitors (PPIs)" are compounds that are inhibit activity of the, $H+/K^+$-adenosine triphosphatase (ATPase) proton pump. A larger number of proton pump inhibitors are well known to those of skill in the art. Certain preferred PPIs include substituted pyridyl methylsulfinyl benzimidazoles. These compounds accumulate in the acid space of the parietal cell and convert to active sulfonamide by an acid-catalyzed reaction. Consequent covalent inhibition of $H^+/K^+$-ATPase blocks the final step of acid secretion. PPIs include, but are not limited to rabeprazole, omeprazole (Prilosec™, Antra™, Audazol™, Desec™, Gastroloc™, Losec™, Miracid™, Mopral™, Zefxon™), lansoprazole ((Prevacid™), and pantoprazole.

The phrase "in conjunction with" when used in reference to the use of proton pump inhibitors in conjunction with pentagastrin indicates that the PPI and the pentagastrin are administered so that there is at least some chronological overlap in their physiological activity on the organism. Thus the PPI and pentagastrin can be administered simultaneously and/or sequentially. In sequential administration there may even be some substantial delay (e.g., minutes or even hours or days) before administration of the second agent as long as the first administered agent has exerted some physiological alteration on the organism when the second administered agent is administered or becomes active in the organism.

The term mammal includes essentially any mammal including, but not limited to dogs, cats, sheep, cattle, horses, goats, mice, rabbits, hamsters, pigs, monkeys and other non-human primates, and humans. Thus, veterinary as well as medical applications of this invention are contemplated.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The phrase "pentagastrin/gastrin/analogue" refers to a pentagastrin, a gastrin, or an analogue or derivative of a gastrin or a pentagastrin, e.g. as described herein.

The phrase "treatment of a pathology" refers to the amelioration or mitigation or elimination of one or more symptoms of the pathology.

BRIEF DESCRIPTION OF THE DRAWINGS

FIG. 1. Calculation of onset and duration. The first arrow indicates the time point when AO falls to <10 mEq/h and the average rate over the next 1 h remains below this value. The second arrow indicates the time point at which AO is >10-mEq/h; the time between arrows is the duration of action value. The time of onset and time span of the longest duration when AO remained >10 mEq/h over the 24-h period was used in the calculation of the mean values. If subjects' AO never fell to <10 mEq/h, the onset was set as missing and duration was set as 0, so as not to bias the mean. Collections were made every 15 min during the first 2 h of the study, then every 30 min after that.

FIG. 5A shows doppler renal artery blood flow (RBF); FIG. 5B shows glomerular filtration rate (GFR); FIG. 5C shows urinary sodium excretion, (UNaV); FIG. 5D shows fractional sodium excretion (FeNa); FIG. 5E shows urinary output, (UV). Each time period shown represents 20 minutes. Within-group comparisons (*, compared to basal, P<0.05) (n=5) were made using analysis of variance (ANOVA), Tukey's test. Between-group comparisons (#) were made using the t-test (#, P<0.05) (n=5). No effect on Mean Arterial Pressure (MAP) was observed during the study period (data not shown).

FIG. 6A shows doppler renal artery blood flow (RBF); FIG. 6B shows glomerular filtration rate (GFR); FIG. 6C shows urinary sodium excretion, (UNaV); FIG. 6D shows fractional sodium excretion (FeNa); FIG. 6E shows urinary output, UV. Each time period shown represents 20 minutes. Within-group comparisons were made using analysis of variance (ANOVA), Tukey's test (*, compared to basal; #, L-365,260 versus vehicle: P<0.05) (n=5). No effect on Mean Arterial Pressure (MAP) was observed during the study period (data not shown).

Figure 7:
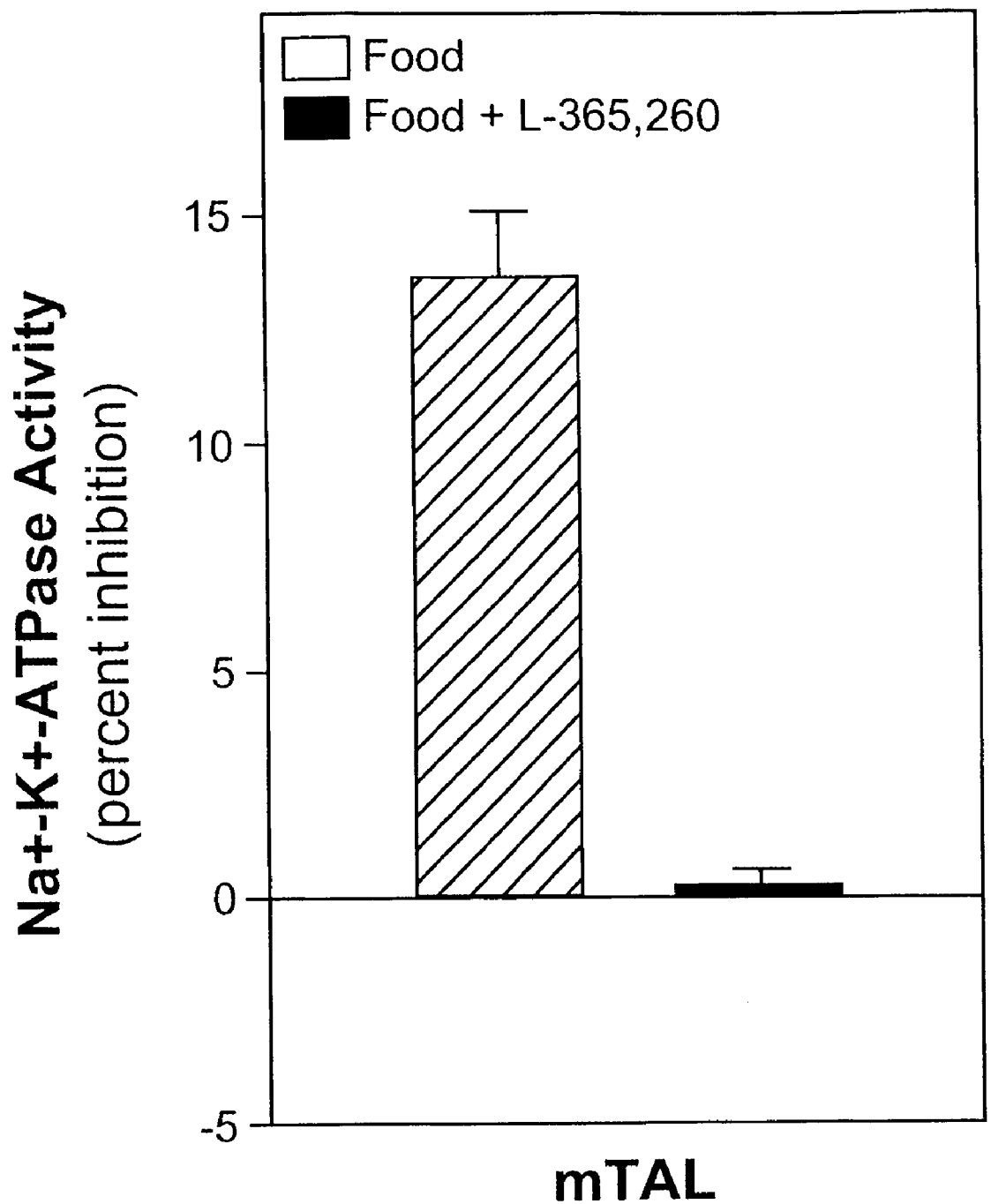

FIG. 7 shows the effect of meal stimulated gastrin on $Na^+$-$K^+$-ATPase activity in the rat proximal tubule and medullary thick ascending limb of Henle. L-365,260 (80 pmoles/kg, 5 min bolus, filled bars, n=6) or vehicle alone (open bars, n=5) was infused into the right renal artery prior to gastrin stimulation by meal gavage with standard rat chow (2.5 ml/hr). $Na^+$-$K^+$-ATPase activity was measured separately in the proximal tubule and medullary thick ascending limb of Henle following the meal. Data are expressed as the mean ±SD of the percent inhibition in $Na^+$-$K^+$-ATPase activity measured in the absence of a meal and with infusion of vehicle alone (n=3).

DETAILED DESCRIPTION

A wide number of pathological conditions are characterized by oversecretion of gastric acid. Such conditions include, but are not limited to Zollinger/Ellison syndrome (ZES), gastroesophageal reflux disease, peptic ulcer disease, duodenal ulcers, atrophic gastritis, esophagitis. In particular, conditions such as ZES and peptic ulcers can have serious complications.

Peptic ulcers are one of the most prevalent diseases in industrialized nations. Control of gastric acid secretion is the main therapy for peptic ulcers. Gastric acid secretion is, in turn, brought about by the interaction of three physiological stimulants, gastrin, acetylcholine and histamine with their respective parietal cell receptors. Prior to the discovery of histamine $H_2$-receptor antagonists such as cimetidine and ranitidine, peptic ulcer treatment consisted of antacid therapy and anticholinergic drugs (e.g. dicyclomine HCl). With the advent of $H_2$-receptor antagonists, however, treatment with anticholinergic agents has been largely supplanted by histamine $H_2$-receptor antagonist therapy. The development of this class of therapeutic entities presents one of the most important advances in the field of medicinal chemistry.

Another major development in the treatment of peptic ulcers has been realized with the introduction of $H^+$/$K^+$-ATPase inhibitors e.g., omeprazole. The enzyme $H^+$/$K^+$-ATPase, which is also known as the proton pump, is located in the membrane of gastric parietal cells and is responsible for the transport of protons from blood to lumen, which, in turn, results in decreasing the pH of stomach contents which leads to aggravation of peptic ulcers.

This invention pertains to the discovery that administration of pentagastrin (an agent that is typically used to increase acid secretion) in conjunction with a proton pump inhibitor (PPI) will result in increased efficacy (e.g. prolonged effect and/or greater effect at reduced dosage) than use of the proton pump inhibitor alone. In particular embodiments, the pentagastrin/PPI combination appears synergistic.

Thus, in one embodiment, this invention provides methods of increasing the efficacy of a gastric $H^+$/$K^+$-ATPase pump inhibitor (PPI) in a mammal (e.g. a rodent, largomorph, bovine, canine, equine, non-human primate, human, etc.). The methods preferably involve administering to the mammal pentagastrin in conjunction with the gastric proton pump inhibitor. The pentagastrin can be administered before, simultaneously with, or after the PPI, but in a most preferred embodiment, the pentagastrin administration precedes the PPI administration.

It was also a discovery of this invention that essentially any increase in gastrin level in conjunction with a PPI will result in increased efficacy of the PPI. Thus, instead of pentagastrin administration, exogenous gastrin can be supplied. Alternatively endogenous gastrin secretion can be upregulated using, for example, aromatic amino acids, or with a meal, etc. Thus, it is believed that essentially anything that stimulates G-cell activity will increase the efficacy of a PPI.

Thus, in various embodiments, this invention contemplates administration of a PPI or combination of PPIs in conjunction with pentagastrin, and/or gastrin, and/or pentagastrin analogues, and/or gastrin analogues to increase the efficacy of the PPI(s).

Proton Pump Inhibitors

Proton pump inhibitors (PPIs) are compounds that are selectively inhibit activity of the gastric acid pump, $H^+$/$K^+$-adenosine triphosphatase (ATPase). Preferred PPIs include substituted pyridyl methylsulfinyl benzimidazoles. These compounds accumulate in the acid space of the parietal cell and convert to active sulfonamide by an acid-catalyzed reaction. Consequent covalent inhibition of $H^+$/$K^+$-ATPase blocks the final step of acid secretion. Other preferred PPIs include various substituted benzimidazoles. Commercially available PPIs include, but are not limited to, omeprazole, lansoprazole, and pantoprazole.

Numerous proton pump inhibitors are known to those of skill. Thus, for example, U.S. Pat. No. 6,093,738 describes novel thiadiazole compounds that are effective as proton pumps inhibitors. European Patent Nos. 322133 and 404322 disclose quinazoline derivatives, European Patent No. 259174 describes quinoline derivatives, and WO 91/13337 and U.S. Pat. No. 5,750,531 offer pyrimidine derivatives, as proton pump inhibitors.

Suitable proton pump inhibitors are also disclosed, for example in EP-A1-0005129, EP-A1-174 726, EP-A1-166 287, GB 2 163 747 and WO90/06925, WO91/19711, WO91/19712, WO94/27988 and WO95/01977.

Particularly preferred PPIs include, but are not limited to omeprazole, lansoprazole, and pantoprazole and derivatives or analogues thereof. One such derivative is s-omeprazole (Nexium™).

The proton pump inhibitors used in the dosage forms of the invention can be used in neutral form or in the form of a salt (e.g., an alkaline salt), such as for instance the $Mg^{2+}$, $Ca^{2+}$, $Na^+$, $K^+$, or $Li^+$ salts, preferably the $Mg^{2+}$ salts. Further where applicable, the compounds can be used in racemic form or in the form of a substantially pure enantiomer thereof, or salts of the racemates or the single enantiomers.

In addition this invention contemplates the use of a single proton pump inhibitor, or in certain embodiments, combinations of two or more proton pump inhibitors.

Proton pump inhibitors are commercially available. In addition, synthesis protocols are well known to those of skill in the art (see, e.g., European Patent Nos. 322133, 404322, 259174, EP-A1-0005129, EP-A1-174 726, EP-A1-166 287, PCT Patent Applications WO 91/13337, WO90/06925, WO91/19711, WO91/19712, WO94/27988 and WO95/01977, U.S. Pat. No. 5,750,531, etc.)

Pentagastrin

Pentagastrin (N-t-butyloxycarbonyl-Beta-alanyl-L-tryptophyl-L-methionyl-L-aspartyl-L-phenyl-alanyl amide, SEQ ID NO:1) is a pentapeptide containing a gastrin carboxyl terminal tetrapeptide, the active portion found in essentially all natural gastrins. Pentagastrin is a colorless crystalline solid soluble in dimethylformamide and dimethylsulfoxide; it is almost insoluble in water, ethanol, ether, benzene, chloroform, and ethyl acetate. Pentagastrin contains the C-terminal tetrapeptide responsible for the actions of the natural gastrins and, therefore, acts as a physiologic gastric acid secretagogue. The recommended dose of 6 µg/kg subcutaneously (in applications where increased gastric acid secretion is desired) produces a peak acid output which is reproducible when used in the same individual. Pentagastrin stimulates gastric acid secretion approximately ten minutes after subcutaneous injection, with peak responses occurring in most cases twenty to thirty minutes after administration. Pentagastrin is typically used as a diagnostic agent for evaluation of gastric acid secretory function. In one preferred formulation, pentagastrin is formulated with sodium chloride and water for injection. The pH is typically adjusted with ammonium hydroxide and or hydrochloric acid. In one commercially available formulation, each ml of injection contains 0.25 mg (250 mcg) pentagastrin along with 8.8 mg sodium chloride and water for injection, USP.

The methods of this invention are not limited to the use of pentagastrin. To the contrary, it was a discovery of this invention that in addition to pentagastrin, exogenous gastrin can be supplied or endogenous gastrin secretion can be upregulated using, for example, aromatic amino acids, or with a meal, etc. Thus, it is believed that essentially anything that stimulates G-cell activity will increase the efficacy of a PPI.

Thus, in addition to gastrin and pentagastrin, this invention contemplates the use of gastrin or pentagastrin analogues or derivatives. Such analogues or derivatives are well known to those of skill in the art. Such variants include, but are not limited to the 34-, 17-, and 14-amino acid species of gastrin, and other truncation variants comprising the active C-terminal tetrapeptide (TrpMetAspPhe-NH$_2$, SEQ ID NO:2) which is reported in the literature to have full pharmacological activity (see Tracey and Gregory (1964) *Nature (London)*, 204: 935). Also included are variants of gastrin and/or truncated gastrins where native amino acids are replaces with conservative substitutions. Also include are various analogues of these molecules, including, but not limited to the N-protected derivative Boc-TrpMetAspPhe-NH$_2$ (SEQ ID NO:3).

In addition, it is noted that gastrins are structurally related to the CCK's are structurally-related neuropeptides which exist in gastrointestinal tissue and in the CNS (see Mutt V., *Gastrointestinal Hormones*, Glass G. B. J., ed., Raven Press, N.Y., p 169 and Nisson G., ibid, 127). Thus it is believed that CCKs or analogues or derivatives thereof that stimulate endogenous gastrin secretion or that generally stimulate G-cell activity will be useful in the methods of this invention.

Gastrins, pentagastrins, or analaogues are commercially available. In addition synthetic protocols are well known. Thus, for example, pentagastrin can be chemically synthesized using well known peptide synthesis methodologies (see, e.g. Barany and Merrifield *Solid-Phase Peptide Synthesis*; pp. 3-284 in *The Peptides: Analysis, Synthesis, Biology*. Vol. 2: *Special Methods in Peptide Synthesis, Part A*.; Merrifield et al. (1963) *J. Am. Chem. Soc.*, 85: 2149-2156; and Stewart et al. (1984) *Solid Phase Peptide Synthesis*, 2nd ed. Pierce Chem. Co., Rockford, Ill.).

Combining PPI and Pentagastrin and, Optionally, Antibiotics

The proton pump inhibitor (PPI) and the pentagastrin (or gastrin or analogue etc.) can be administered simultaneously. However, in a preferred embodiment, the pentagastrin or analogue thereof is administered first followed by the PPI. In certain embodiments, the pentagastrin or analogue thereof can be administered after the PPI.

The methods of this invention are not limited to the use of a single pentagastrin/analogue or to the use of a single PPI. In certain embodiments, combinations of two or more PPIs and/or two or more pentagastrin/analogues are contemplated.

In certain embodiments, it is desirable to administer one or more antibiotics in conjunction with the PPI and pentagastrin. Thus, for example, the treatment of ulcers associated with *Helicobacter* sp infection (e.g. *Helicobacter pylori*), the antibiotic will mitigate/eliminate the bacterial component of the pathology.

It is noted that U.S. Pat. No. 5,629,305 teaches that a proton pump inhibitor (e.g. omeprazole or lansoprazole) which increases intragastric pH, can increase the bioavailability of various antibiotics, in particular the therapeutic amount of an acid degradable antibacterial compound such as a penicillin or a macrolide. A wide variety of antibiotics are suitable for use with the methods of this invention. Such antibiotics include, but are not limited to penicillin based antibiotics, tetracyclines, macrolides, cephalosporins, fluoroquinolones, and the like.

Pharmaceutical Formulations and Administration Thereof

The gastrin and/or pentagastrin or derivatives or analogues thereof, and/or PPI(s) used in the methods of this invention, (e.g. the therapeutic catalytic antagonists) are preferably administered by intravenous, parenteral, or oral means. The active molecules (e.g., PPI or pentagastrin) are typically combined with a pharmaceutically acceptable carrier (excipient) to form a pharmacological composition. Pharmaceutically acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the route of administration of the PPI/pentagastrin and on the particular physio-chemical characteristics of the agent.

In various embodiments the gastrin/pentagastrin/analogue and/or the PPI can be provided in a substantially dry and/or pure form to be combined with a diluent/excipient at the time of use or one or both agents can be provided already combined with an appropriate excipient (e.g. in a unit dosage form). In certain embodiments, the gastrin/pentagastrin/analogure or the PPI is provided in a dry (e.g. lyophilized/dehydrated) form, while the other component is suspended in a fluid excipient. Addition of the dry component to the excipient results in the admixture of the gastrin/pentagastrin/analogure and the PPI. In other embodiments, both the pentagastrin and the PPI are provided combined in a compatible excipient.

It is noted that, in certain embodiments, the PPI and the gastrin/pentagastrin/analogue can be provided combined with different excipients but in a single unit dosage form. Thus, for example, a tablet can comprise two lamina, one lamina containing the pentagastrin and a first excipient and the second lamina containing the PPI and a second excipient. If necessary the lamina can be separated by an inert/neutral layer. Other "multi-excipient" systems can be similarly formulated (e.g. as time release particles in a capsule, dual container gelatin capsules, etc.).

Thus, the pharmaceutical compositions can be administered in a variety of unit dosage forms depending upon the method of administration. For example, unit dosage forms suitable for oral administration include powder, tablets, pills, capsules and lozenges. Certain therapeutic molecules of this invention may be only marginally soluble in aqueous solutions. In a preferred embodiment, these compositions are typically solubilized, emulsified or suspended in an acceptable excipient.

It is noted that pharmaceutically acceptable formulations for pentagastrin and PPIs are well known to those of skill in the art. Thus, the PPI and the pentagastrin can be administered in the formulation(s) and by the means typically used for these drugs. In particularly preferred embodiments, the pentagastrin is administered by subcutaneous injection.

The concentration of therapeutic agent in these formulations can vary widely, and will be selected primarily based on fluid volumes, viscosities, body weight and the like in accordance with the particular mode of administration selected and the patient's needs. Actual methods for preparing administrable compositions will be known or apparent to those skilled in the art and are described in more detail in such publications as *Remington's Pharmaceutical Science*, 15th ed., Mack Publishing Company, Easton, Pa. (1980).

Dosages for typical therapeutics, particularly for PPIs, are well known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient.

In preferred embodiments, the pentagastrin and PPI will be administered in an amount sufficient to effect a measurable decrease in gastric acid secretion, more preferably in an amount sufficient to effect a significant decrease in gastric acid secretion (e.g., a statistically significant decrease at the 90%, more preferably at the 95%, and most preferably at the 98% or 99% confidence level). The pentagastrin dosage will range from about 0.05 to about 0.05 to about 25 µg/kg/hr, preferably from about 0.1 µg/kg/hr to about 15 µg/kg/hr and most preferably from about 0.5 µg/kg/hr to about 10 µg/kg/hr, while the PPI dosage, in preferred embodiments, will be consistent with current clinical practice.

Similarly, where the pentagastrin and PPI are administered in combination with an antibiotic, the antibiotic is typically administered in a manner and concentration consisting with clinical practice.

Uses of PPI and Pentagastrin Combinations

The proton pump inhibitors are, as already mentioned, useful for inhibiting gastric acid secretion in mammals and man. In a more general sense, they may be used for prevention and treatment of gastric-acid related diseases in mammals and man, including e.g. reflux esophagitis, gastritis, duodenitis, gastric ulcer and duodenal ulcer. Furthermore, they may be used for treatment of other gastrointestinal disorders where gastric acid inhibitory effect is desirable, e.g. in patients on NSAID therapy, in patients with Non Ulcer Dyspepsia, in patients with symptomatic gastro- esophageal reflux disease, and in patients with gastrinomas. They may also be used in patients in intensive care situations, in patients with acute upper gastrointestinal bleeding, pre- and postoperatively to prevent aspiration of gastric acid and to prevent and treat stress ulceration. Further, they may be useful in the treatment of Helicobacter infections and diseases related to these. Other conditions well suited for treatment according to the methods of this invention include, but are not limited to Zollinger-Ellison syndrome (ZES), Werner's syndrome, and systemic mastocytosis.

The methods and formulations of this invention are suitable for use in essentially any mammal and this invention embraces veterinary as well as human medical applications. Thus, the methods of this invention are applicable to humans and non-human mammals (e.g. a rodent, largomorph, bovine, canine, equine, non-human primate, etc.).

Therapeutic Kits

In another embodiment, this invention provides therapeutic kits for practice of the methods of this invention. Such kits preferably include a container containing one or more proton pump inhibitor(s) and a container containing pentagastrin and/or a pentagastrin/gastrin analogue or derivative. Both the pentagastrin and the PPI(s) can be in one container or they can be in separate containers. In certain embodiments, the "pentagastrin/gastrin/analogue" and/or the PPIs are provided in a dry form, while in other embodiments, the "pentagastrin/gastrin/analogue" and/or PPIs are suspended, or dissolved in an excipient/buffer.

In certain embodiments, the kits optionally include one or more antibiotics, e.g. an antibiotic selected from the group consisting of penicillin based antibiotics, tetracyclines, macrolides, cephalosporins, and fluoroguinolones.

The kit can comprise packaging that retains and presents the medicants at separate respective consecutive locations identified by visibly discernible indicia and the times at which the medicants are to be taken by the patient. In various embodiments, the times can include each day of the week and specified times within each day presented in the form of a chart located on one face of the package wherein the days of the week are presented and the times within each day the medicants are to be taken are presented in systematic fashion.

In addition, the kits can include instructional materials containing directions teaching the use of a pentagastrin, a gastrin, or a derivative or analogure thereof in combination with one or more PPIs to enhance the efficacy of the PPI. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Inhibition of Pentagastrin-Induced Gastric Acid Secretion by Intravenous Pantoprazole: A Dose-Response Study The purpose of this study was to compare the gastric acid inhibitory ability of increasing doses of intravenous (i.v.) pantoprazole with that of i.v. famotidine and placebo. Pentagastrin was infused continuously in healthy subjects as a model for patients with Zollinger-Ellison syndrome.

In brief, pentagastrin (1 μg/kg/h) was infused to stimulate maximum acid output in 39 subjects over a 25-h period. After 60 min of pentagastrin infusion, subjects received a single dose of i.v. pantoprazole (20, 40, 80, or 120 mg), i.v. famotidine (20 mg), or saline placebo. The variables measured were onset of response (time until acid output fell to <10 mEq/h), duration of response (time acid output remained <10 mEq/h), and cumulative acid output over 24 h.

All doses of i.v. pantoprazole produced a dose-dependent suppression of acid output to <10 mEq/h. Single i.v. doses of pantoprazole, 80 and 120 mg, suppressed acid output by >90% in all subjects for ≦21 h and had an onset of action of <1 h. Intravenous pantoprazole had a rapid onset and a clear dose-related effect, with a significantly longer duration of action than that of i.v. famotidine.

Introduction.

Zollinger/Ellison syndrome (ZES), a gastric hypersecretory condition that results from high circulating levels of gastrin, often requires high and repeated doses of acid output (AO) inhibiting agents to reduce effectively intragastric acidity. Although histamine H2-receptor antagonists have been used successfully to treat ZES in the past, the erratic and diminishing responses with theses antagonists (McCarthy and Hyman (1982) *Dig. Dis. Sci.*, 27: 353-357), as well the progressive occurrence of more severe side effects associated with the use of larger doses (Drogen et al. (1978) *Drugs*, 15: 93-131), has led to the use of more effective proton pump inhibitors (PPIs).

Parenteral antisecretory drugs are often required in patients with ZES who have nausea, vomiting, or severe diarrhea (Von Schrenck et al. (1988) *Gastroenterology*, 1326-1334; Fox et al. (1974) *Surg. Clin. North. Am.*, 54: 395-407). This occurs during the preoperative period, during the administration of chemotherapy and in the setting of upper gastrointestinal bleeding. However, currently there are no intravenous (i.v.) dosage forms of PPIs approved for use in the United States. Although effective in high doses, i.v. H2-receptor antagonists must be continuously infused, which is not always possible in ZES patients (Saced et al.(1989) *Gastroenterology*, 96: 1393-1402; Fraker et al. (*Surgery*, 104: 1054-1063).

Pantoprazole, the newest PPI, has been shown to be as potent when administered by the i.v. route as by the oral route in short term studies (Hartmann and Ehrlich (1998) *Aliment. Pharmacol. Ther.*, 12: 1027-1032; Simon et al. (1990) *Aliment Pharmacol. Therap.*, 4: 239-245). However, no i.v. dose-response studies have previously been performed during the continuous administration of i.v. pentagastrin over a 24-h period. We attempted to extend the knowledge obtained from a previous study (Simon et al. (1990) *Z. Gastroenterol.*, 28: 443-447) to a 24 h and to predict the minimum effective, single i.v. dose of pantoprazole needed to control AO in patients with ZES, by developing a continuous pentagastrin infusion model that would stimulate maximal gastric AO and thereby mimic ZES in healthy volunteers.

The intent of this study is to provide an informative pharmacological model for the management of ZES by predicting the minimum effective does of i.v. pantoprazole needed to control AO, and to compare the efficacy and duration of various single doses of i.v. pantoprazole with those of single doses of i.v. famotidine (20 mg) and placebo to suppress pentagastrin (PG)-stimulated AO over a 24-h period.

Materials and Methods

A total of 39 healthy men and women, 18-45 yr of age (mean age, 31.4±6.7 yr:male/female ratio, 2:1), were selected for this open label, single dose, single site, parallel treatment study. The study protocol was approved by the UCLA Institutional Review Board and conducted according to the provisions of the Declaration of Helsinki and its amendments. Written informed consent was obtained from each participant before enrollment, and the identity of each patient was kept confidential.

Each subject underwent a prestudy screening that included a physical examination, electrocardiogram (ECG), laboratory blood and urine analysis, and a pregnancy test for women. The laboratory test included a complete blood count, blood chemistry tests, a test for human immunodeficiency virus, a screening for hepatitis B and C, and a urine drug screen. Subjects were excluded from the study if abnormalities in these parameters were detected. Maximum AO (MAO) were also determined during the screening period. MAO was estimated by the subcutaneous injection of PG (6 μg/kg), after which four 15-min samples were collected and analyzed (Table 1). Subjects who were huposecretors (MAO <5 mEq/h), who tested positive for *Helicobacter pylori* (*H. pylori*), or who had a history of peptic ulcer disease were excluded from the study. Subjects who completed the screening examination and were eligible for the study were assigned to one of six treatment groups to receive i.v. doses of pantoprazole (20, 40, 80, or 120 mg), i.v. famotidine (20 mg), or placebo (normal saline). Pantoprazole (manufactured by Byk Gulden and supplied by Wyeth-Ayerst Research) in the form of lyophilized powder (40 mg) was reconstituted with normal saline in a quantity sufficient to make 90 ml.

To stimulate MAO, subjects received an infusion of PG for 25 h (Peptavalon, Wyeth-Ayerst; 1.0 μg/kg/h) begun 1 h before the start of the study drug infusion. Gastric aspirates were collected by means of nasogastric (NG) tube in 15-min fractions from 1 h before study drug treatment through the end of treatment h 2 and in 30 min fractions from h 3 through the end of h 24.

TABLE 1

Acid output values after intravenous treatment.

| Treatment | Screening Period (MAO) | Acid Output (mEq/h) | | Treatment Period | | |
|---|---|---|---|---|---|---|
| | | −1-0 h | 0-6 h | 6-12 h | 12-18 h | 18-24 h |
| Pantoprazole (mg) | | | | | | |
| 20 (n = 4-6) | 36.6 ± 9.0 | 18.8 ± 8.8 | 11.7 ± 10.5 | 13.6 ± 13.3 | 15.1 ± 13.7 | 14.2 ± 8.6 |
| 40 (n = 8) | 40.1 ± 7.8 | 22.3 ± 13.0 | 8.1 ± 5.4 | 4.8 ± 4.0 | 7.3 ± 4.1 | 10.1 ± 3.7 |
| 80 (n = 8) | 27.1 ± 4.5 | 18.8 ± 17.4 | 2.4 ± 1.5 | 1.2 ± 0.6 | 3.7 ± 1.9 | 6.1 ± 3.2 |

TABLE 1-continued

Acid output values after intravenous treatment.

| Treatment | Screening Period (MAO) | Acid Output (mEq/h) | | Treatment Period | | |
|---|---|---|---|---|---|---|
| | | −1-0 h | 0-6 h | 6-12 h | 12-18 h | 18-24 h |
| 120 (n = 4-5) Famotidine (mg) | 16.9 ± 3.6 | 6.9 ± 4.8 | 1.3 ± 0.8 | 0.7 ± 0.2 | 3.7 ± 0.7 | 5.2 ± 0.4 |
| 20 (n = 4) | 28.1 ± 7.0 | 29.1 ± 15.4 | 4.4 ± 2.5 | 17.7 ± 5.1 | 25.8 ± 9.3 | 25.0 ± 10.4 |
| Placebo (n = 3-8) | 42.8 ± 5.6 | 35.2 ± 9.3 | 34.1 ± 8.7 | 35.8 ± 8.7 | 34.8 ± 2.2 | 33.1 ± 9.6 |

Figure 1:
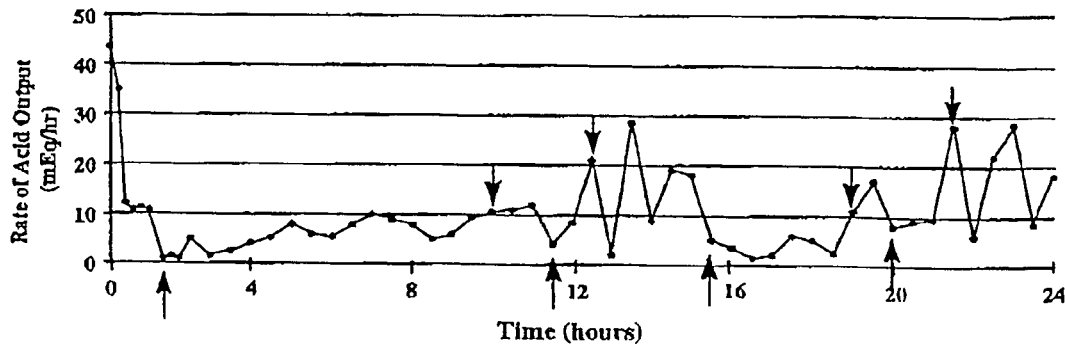

The variables measured were onset of response (time until AO decreased to <10 mEq/h and remained below this level for 1 h), duration of response (time from onset until time when AO levels rose to >10 mEq/h and remained so for 1 h), and cumulative AO over 24 h. The method of calculating onset and duration are shown in FIG. 1. The mean percent inhibition of acid production at the study periods of 0-6 h, 6-12 h, 12-18 h, and 18-24 h was calculated for each study group. The percent inhibition was determined by comparing each group's mean pretreatment MAO to the mean AO during the above study drug periods by using the following formula:

% inhibition=11−average rate of MAO over time indicated/average AO in the period before study drug administrational (100%)

On the evening before study day 1, participants were admitted to the UCLA Clinical Research Center. The following morning (study day 1), after nasogastric (NG) tube placement and the basal collection period, subjects were started on continuous i.v. PG administration and MAO analyses were performed. At the end of this period a single dose of pantoprazole, famotidine, or placebo was infused in the opposite arm over 15-min. Because no fluid or food p. o. was permitted during the study period, subjects received maintenance i.v. fluid to prevent dehydration. Vital signs and electrolytes were monitored during this time. On the morning of study day 2, at the end of the 25-h period, participants underwent a post study evaluation that included a physical examination, an ECG, and analyses of blood and urine.

The efficacy of the response to pantoprazole or famotidine was determined by measuring levels of gastric acid secretion by using standard collection and assay techniques (White et al. (1973) *Dig. Dis.,* 18: 7-13). Because this was an exploratory study, statistical analysis consisted of presenting means and standard deviations.

Adverse events were monitored continuously in the Clinical Research Center. Treatment-emergent adverse events were defined as adverse events not present at baseline or events present at baseline that worsened during treatment.

Results

Model

Figure 2:
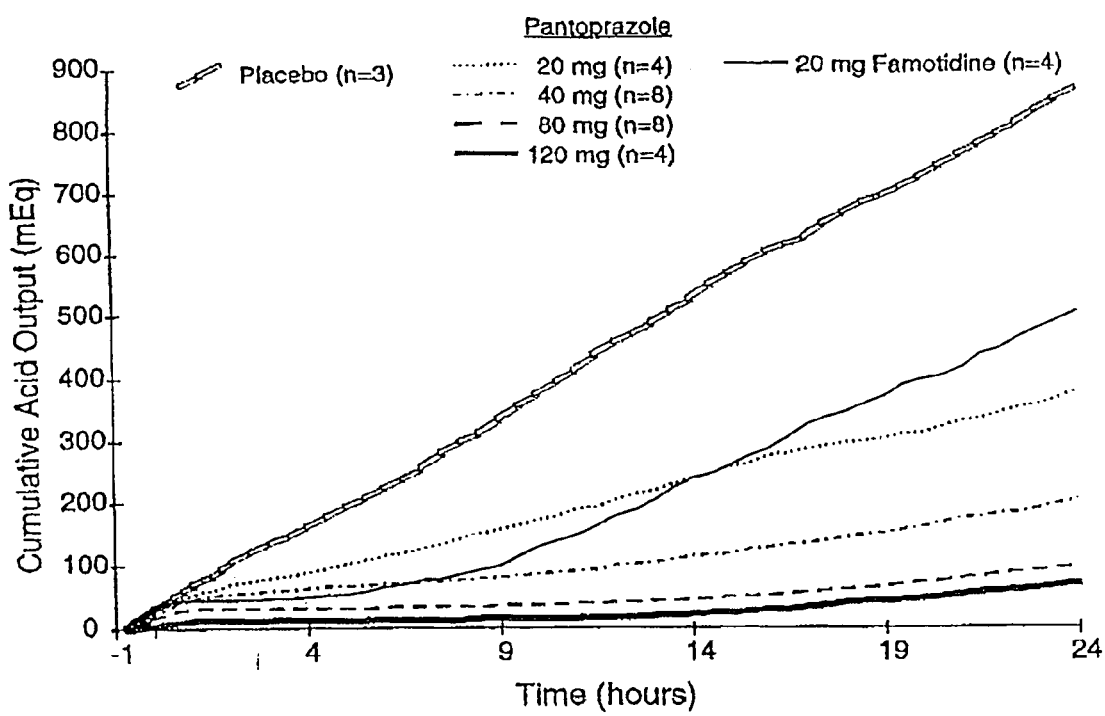
FIG. 2. Mean cumulative AO over the 25-h period after a single i.v. dose of pantoprazole (20, 40, 80, and 120 mg), i.v. famotidine (20 mg), or placebo. Note that AO remained constant for the placebo group over the entire 25-h period of PG administration.
Figure 3:
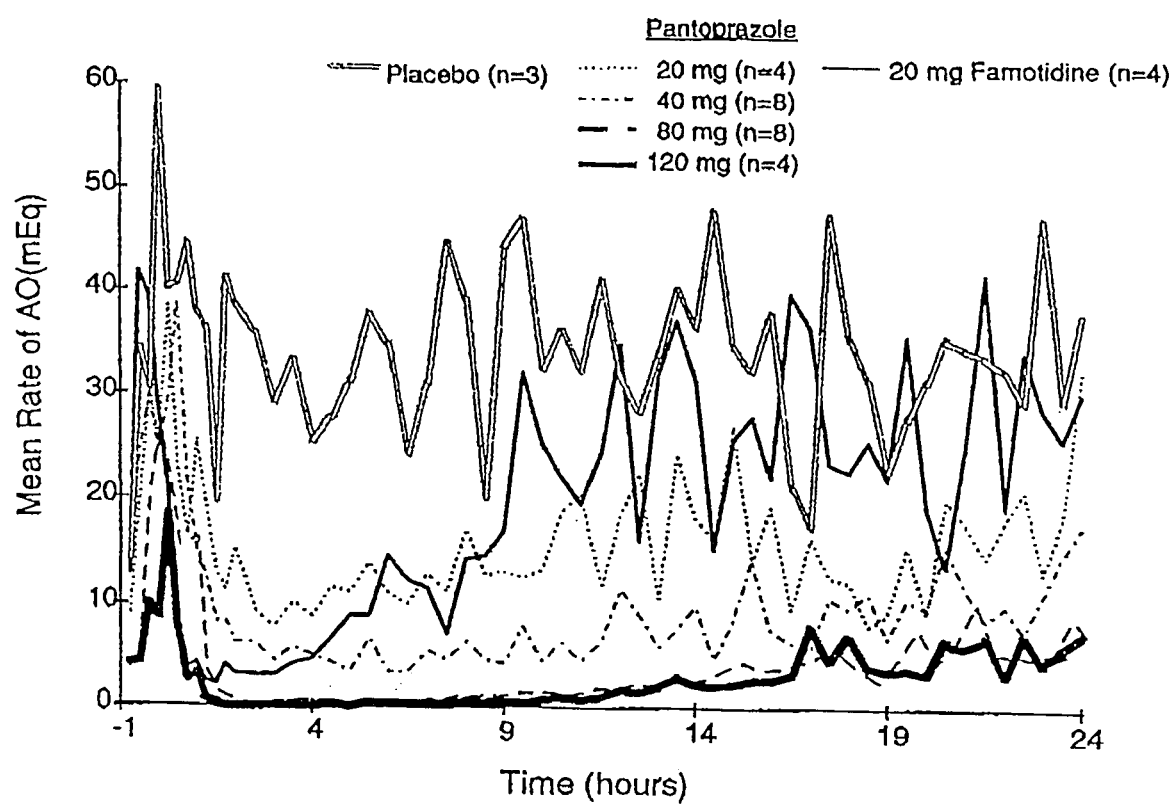
FIG. 3. Mean rate of AO over 24 h for IV pantoprazole (20, 40, 80, or 120 mg), i.v. famotidine (20 mg), or placebo.

During the screening period, a single subcutaneous injection of PG elevated acid output in all groups (Table 1). All MAO values appeared normal in this healthy population of volunteer subjects. The continuous infusion of PG produced a significant and constant increases in AO during the study. Mean cumulative AO increased in a linear fashion in the placebo group over the 25-h period of PG stimulation (FIG. 2). After an initial burst of AO after the start of stimulation, AO fluctuated between 20 and 50 mEq/h (mean, 34.5 mEq/h) during the course of the study (FIG. 3). Cumulative AO (0-24 h) reached a mean value of 829±86 mEq. There was no evidence of tachyphylaxis to the gastric acid-stimulating effects of PG.

Onset

Figure 4A:
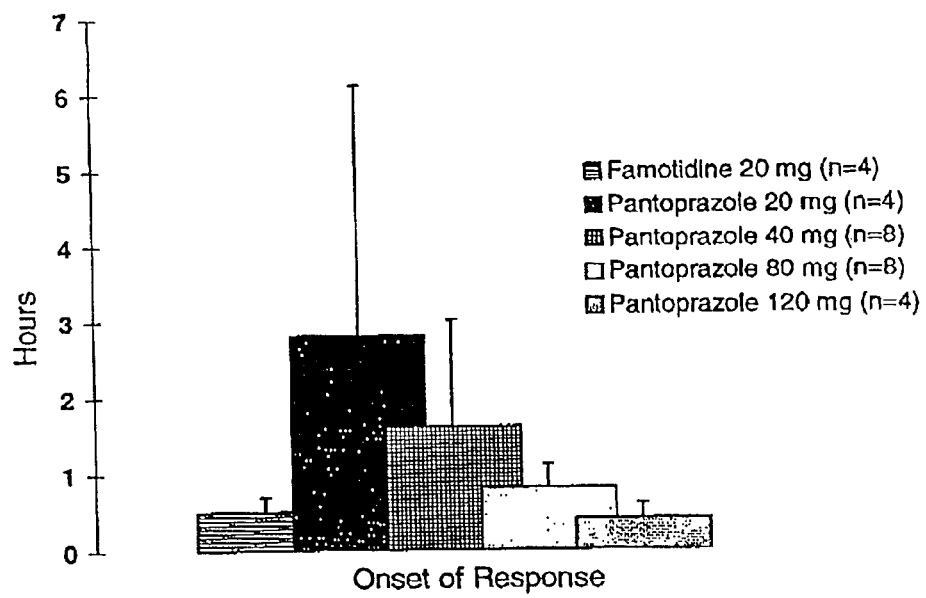
FIG. 4A shows meantime of onset and FIG. 4B shows duration of response for escalating doses of i.v. pantoprazole or a single i.v. dose of famotidine. Onset of response is defined as time until AO decreased to <10 mEq/h and remained below this level for 1 h. Duration of response is defined as time from onset until time when AO levels rose to >10 mEq/h and remained so for 1 h. Values are mean ±SD.

In general, the acid-suppressing activity of pantoprazole was observed within 15-20 min after administration. All doses of pantoprazole suppresses AO to <10 mEq/h (FIG. 3). The onset of response (mean ±SD) was <1 h (0.8±0.3 h) for 80 mg pantoprazole, which was approximately equal to that seen with high dose i.v. famotidine (0.5±0.2 h) (FIG. 4A). Onset was faster with the 120-mg pantoprazole dose (0.4±0.2 h); however, the difference was not significant.

Duration

Figure 4B:
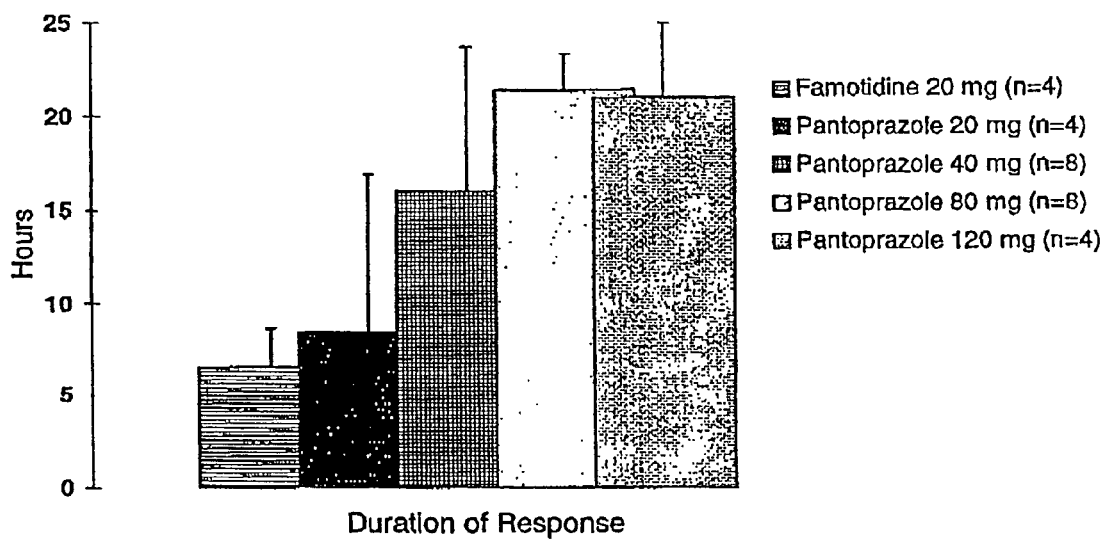

AO values (mean ±SD) at periods of 0-6 h, 6-12 h, 12-18 h, and 18-24 h after i.v. treatment are shown in Table 1. Peak inhibition was reached at approximately 3-43 h for all doses: 83% inhibition in the 20-mg dose group, 90% inhibition in the 40-mg dose group, 99% inhibition in the 80-mg dose group, and 100% inhibition in the 120-mg dose group. Peak inhibition was 94% for famotidine. The duration of action for 80 mg of pantoprazole was markedly longer (21.2±1.9 h) than with 20 mg (8.4±8.0 h), 40 mg (15.9±7.6 h) of pantoprazole, or 20 mg (6.5±2.1 h) of famotidine (FIG. 4B). Although 40 mg pantoprazole suppresses AO for approximately 16 h, the time to onset and duration of action were more variable among individual subjects in this dose group compared with those subjects given 80 and 120 mg of pantoprazole. The doses of pantoprazole with >90% inhibition (i.e., 40, 80, 120 mg) had no longer durations of action than did 20 mg of famotidine.

Average AO Over 24-h Period

After 1 h, both the 80 and the 120-mg doses of pantoprazole suppressed AO to <10 mEq/h in all subjects, where it remained for the full 24-h period (FIG. 2), whereas famotidine lost effectiveness after 6 h. Intravenous pantoprazole reduced cumulative AO in a dose-dependent manner. When averaged over the 24-h period, a dose of 20 mg and 40 mg pantoprazole reduced the hourly AO to 11.9 mEq/h and 7.6 mEq/h respectively. The lowest average rate over the 24 h was seen in the 120 mg group (2.4 mEq/h), followed closely by 80 mg pantoprazole (3.3 mEq/h). Famotidine had an average ratio over the 24-h period of 18.2 mEq/h.

Safety

Of the 39 subjects enrolled, 35 completed the study. There were no serious adverse events observed. The most frequently reported adverse events were dyspepsia, which was mild in most cases, and mild gastric bleeding. Four subjects withdrew from the study because of there adverse events. Three subjects receiving i.v. pantoprazole withdrew from the study because of increasing dyspepsia or nausea, and one receiving placebo withdrew because of dyspepsia and bleeding. No subjects from the famotidine group withdrew because of adverse events. Three subjects from the famotidine group complained of abdominal pain and dyspepsia and were noted to have small amounts of blood in their NG aspirate. None of the adverse events were judged by the investigator to be related to any of the study drugs and could have been due to the administration of i.v. pentagastrin. All subjects' symptoms disappeared shortly after discontinuations of the study. No clinically important abnormal laboratory results or other findings, including ECGs, were reported. None of the subjects reported visual changes.

Discussion

The results of this study demonstrated that single doses of i.v. pantoprazole ranging from 20 mg to 120 mg suppressed gastric acid secretion, in a dose-dependent manner, to <10 mEq/h in healthy volunteers subjects to continuous PG-induced hypersecretion. The doses of pantoprazole producing >90% inhibition (i.e., 40, 80, and 120 mg) had a longer duration of action than did famotidine. Although famotidine effectively reduced AO, it had a relatively short duration of action compared with that of pantoprazole. Pantoprazole doses of 80 mg and 120 mg had an onset of action <1 h and suppresses acid output (99-100%) to <10 mEq/h for >20 h. No difference in cumulative gastric acid output was observed between the group receiving 80 mg and that receiving 120 mg of pantoprazole. These data suggest that a single dose of 80 mg i.v. pantoprazole will rapidly and effectively control acid secretion in most patients with gastric acid hypersecretory states, such as those who have ZES.

Because the clinical manifestations of ZES, including death, are almost entirely due to the effects of hypergastrinemia (Fox et al. (1974) *Surg. Clin. North. Am.*, 54: 395-407; Ellison and Wilson (1964) *Ann. Surg.*, 160: 512-530; Jensen et al. (1983) *Ann. Intern. Med.*, 989: 59-75), a reduction of AO to normal levels, i.e., <10 mEq/h, has proved to be an effective treatment and prolongs survival. In some situations, however it is advantageous to inhibit gastric acid secretion via the i.v. route of administration: for example, in unconscious ZE patients, those with upper gastrointestinal bleeding, or in patients with metastatic disease receiving chemotherapy (Von Schrenck et al. (1988) *Gastroenterology*, 1326-1334). Thus, there is an urgent need for a parenteral antisecretory drug that can reduce AO, safely and effectively, to clinically tolerable levels. Currently there are no i.v. forms of PPIs approved for use in the United States. Although the histamine H2 receptors antagonists cimetidine (Ronfils et al. (1979) *World J. Surg.*, 3: 597-604; McCarthy (1978) *Gastroenterology*, 74: 453-458), ranitidine (Howard et al. (1985) *Gastroenterology*, 88: 1026-1033), and famotidine (Howard et al. (1985) *Gastroenterology*, 88: 1026-1033; Campoli-Richards (1986) *Drugs*, 32: 197-221) effectively and safely control gastric acid hypersecretion in patients with ZES, they all have certain disadvantages; these include the need for high and more frequent dosing (Rume et al. (1981) *Gastroenterology*, 80: 1265), the occurrence of tachyphylaxis (Devency et al. (1983) *Am. J. Surg.*, 146: 116-123), the need for continuous i.v. infusion (Saced et al.(1989) *Gastroenterology*, 96: 1393-1402; Fraker et al. (*Surgery*, 104: 1054-1063), and lack of response in some patients (Drogen et al. (1978) *Drugs*, 15: 93-131; Vallot et al. (1983) *Dig. Dis. Sci.*, 28: 577-584). The rapid loss of antisecretory efficacy with these agents may account for the failure in the treatment of patients with ZES syndrome, in which high doses of H2-recepor antagonists must be used. In our study, all doses of pantoprazole had a longer duration of action than did famotidine and, thus, would appear to be preferable to i.v. famotidine for controlling gastric acid secretion in patients with ZES.

In addition, our investigation showed that i.v. PG (1 pg/kg/h) administered for ≦25 h created a continuous hypersecreory acidic environment with no indication of tachyphylaxis, as evidenced by the increase in gastric acid secretion at the end of the 24-h period for all subjects in all treatment groups, including the placebo group. This study was one of the first to use PG for a 25-h duration and extends the time length of a previous 4-h study (Simon et al. (1990) *Z. Gastroenterol.*, 28: 443-447). Results using healthy subjects have shown that 80% maximal gastric secretory response is reached in approximately 80% of subjects given a PG dose of 0.6 μg/kg/h (Mason et al. (1969) *Gut*, 10: 34-38; Wormsley et al. (1966) *Lancet*, 1: 993-996). The dose of 1 pg/kg/h was chosen because it is tolerable and produces a near maximal acid secretion that is sustainable for 24 h in healthy subjects and that is comparable to the lower range of AO seen in patients with ZES (Mason et al. (1969) *Gut*, 10: 34-38; Wormsley et al. (1966) *Lancet*, 1: 993-996; Chin et al. (1986) *J. Clin. Pharmacol.*, 26: 281-285). This PG stimulation model has been shown to be particularly relevant to the study of the Zollinger-Ellison syndrome (Hirschowitz et al. (1995) *Dig. Dis. Sci.*, 40(suppl): 3S-23S).

There were no serious adverse events in this study. The most frequently reported event was mild to moderate dyspepsia. This was experienced by subjects who were administered the pantoprazole 20-mg dose, i.v. famotidine, or placebo, and was probably due to the unopposed effects of gastric acid secretion, or to PG or NG tube protocol procedures. A small number of subjects were noted to have modest amounts of blood in their NG aspirate; however, this was believed to be related to NG tube trauma or to the effects of continuous pentagastrin.

In conclusion, these results indicate that a single dose of i.v. pantoprazole rapidly and effectively reduces gastric acid secretion in a dose-dependent manner to normal levels in subjects exposed to continuous i.v. PG infusion. A single dose of i.v. pantoprazole, either 80 mg or 120 mg, reduced AO levels as quickly and more potently than did i.v. famotidine 20 mg, and had a duration of action approximating 24 h. Furthermore, these data predict that gastric acid secretion can by safely and effectively controlled by i.v. pantoprazole at a dose of 80 mg in patients with gastric acid hypersecretory disorders such as ZES, and that i.v. pantoprazole is preferable to i.v. famotidine. Although, in this study, i.v. pantoprazole rapidly and effectively inhibited gastric acid secretion in subjects following stimulated conditions such as with i.v. pentagastrin, its efficacy in unstimulated conditions such as in intensive care settings was not assessed here, but deserves further investigation.

Example 2

Discovery of Gastrin Receptors in the Kidney Reveals Hormonal Coupling of Digestion and Excretion Ingestion of a meal results in acute changes in renal function necessary to handle absorbed nutrients (Pullman (1954) *J. Lab. Clin. Med.* 44: 320-332; Jolliffe and Smith (1931) *Am. J. Physiol.* 99: 101-107; Schoolwerth et al.

(1975) *Kidney Int.* 7: 397-404). However, the mechanism for communication between the digestive and renal systems has never been established. In this example, we report that receptors for gastrin, cholecystokinin type B/gastrin receptors (CCKB/gastrin), are expressed at high levels in the kidney and that gastrin, elevated by either a meal or direct renal infusion, stimulates an increase in urinary $Na^+$ excretion and urine volume that is inhibited by the CCKB/gastrin receptor-specific antagonist, L-365,260 (Lotti and Chang (1989) *Eur. J. Pharmacol.* 163: 273-279). Gastrin stimulated excretion of sodium and water and its reversal by L-365,260 are paralleled by CCKBR/gastrin receptor mediated inhibition and reversal of inhibition of renal tubular $Na^+$-$K^+$-ATPase activity, respectively. The identification and functional characterization of renal tubular gastrin receptors reveals the direct link between digestion and renal excretion mediated by the principle meal-stimulated gastrointestinal hormone, gastrin.

Introduction

Nutrients absorbed during a meal present an acute load to the kidneys that are responsible for maintaining tight control of metabolites including water and electrolytes. It has been hypothesized for many years that gastrointestinal hormones that become elevated in response to a meal may play a role in the acute regulation of the renal handling of absorbed nutrient (Reinhardt et al.: (1975) *Pflugers Arch.* 354: 287-297; DeSanto et al. (1992) *Ren. Physiol. Biochem.* 51: 53-56; Bosch et al. (1983) *Am. J. Med.* 77: 873-879; Hostetter (1986) *Am. J. Physiol.* 250: F613-F618). Although several gastrointestinal hormones have been shown to indirectly influence renal function at pharmacologic concentrations, the actual meal stimulated hormones that are physiologically responsible, as well as their site and mechanism of action, have remained elusive. In humans, renal responses to protein meal ingestion led to a significant increase in the glomerular filtration rate (GFR), renal plasma flow (RPF) and an increase in salt excretion suggesting that these effects were related to the ingestion of the protein meal (DeSanto et al. (1992) *Ren. Physiol. Biochem.* 51: 53-56; Hostetter (1986) *Am. J. Physiol.* 250: F613-F618). We hypothesized that gastrin, released following protein meals, may account for the renal responses observed in these investigations.

Previous studies have identified that the kidney is a major site for gastrin excretion that is not dependant on degradation of the peptide (Davidson et al. (1973) *Gastroenterology* 64: 955-961). A positive correlation between the renal functional mass and the ability of the kidney to extract gastrin support the role of the kidney as an organ with an important role in gastrin clearance (Kes et al. (1993) *Renal Physiol. Biochem.* 16: 268-275). This role of the kidney in the ability to clear gastrin has been best exemplified by the observation of an increase in serum gastrin following nephrectomy in the rat (El Munshid et al. (1980) *J. Physiol.*, 299: 157-171). Similarly, in humans there is a significant increase in the serum levels of gastrin once the serum creatinine is elevated >3.0 mg/dl (Hansky (1979) *World J. Surg.* 3: 463-467) that is reversed following renal transplantation (Nieksen et al. (1980) *Acta Med. Scand.* 207: 85-87).

The primary role of gastrin is believed to be in the regulation of gastric acid secretion. Gastrin is released by gastric antral and intestinal G-cells into the circulation following a meal and remains elevated for up to two hours. Previous studies have identified the kidney as a major site for gastrin excretion that is not dependant on degradation of the peptide (Schjonsby and Willassen (1977) *Scand. J. Gastroenterol.*, 12: 205-207; Davidson et al. (1973) *Gastroenterology* 64: 955-961). Following the cloning of the CCKB/gastrin receptor (Wank et al. (1992) *Proc. Natl. Acad. Sci., USA,* 89: 8691-8695), receptor tissue distribution studies unexpectedly revealed a high level of both receptor mRNA and protein in the kidney. This finding immediately suggested a physiologic role for meal stimulated gastrin in the regulation of renal excretion. The CCKB/gastrin receptor is a heptahelical, guanine nucleotide binding regulatory protein-coupled receptor known to couple via Gαq to the activation of phospholipase C with the subsequent formation of inositol phospholipids and the release of intracellular calcium (Wank et al. (1992) *Proc. Natl. Acad. Sci., USA,* 89: 8691-8695). To date, there have been no studies linking the CCKB/gastrin receptor to the activation of Na+/K+ ATPase.

In this example, we demonstrate that CCKB/gastrin receptors are highly expressed in the kidney in an anatomic distribution functionally consistent with the actions of gastrin on the kidney. Physiologic concentrations of gastrin either infused or naturally elevated in response to a meal act specifically at CCKB/gastrin receptors on renal tubular cells to increase the excretion of salt and water into the urine. Specific antagonism of meal stimulated gastrin indicates that gastrin is the predominant mediator effecting meal induced renal excretion. The observed gastrin related inhibition of renal tubular $Na^+$-$K^+$-ATPase activity may account for the mechanism of its actions. The discovery and functional characterization of renal tubular CCKB/gastrin receptors strongly suggests that gastrin is the principle mediator coupling digestion and renal exretion.

Materials and Methods

Immunohistochemistry

Rat kidney sections were cut, fixed in 4% formaldehyde in PBS for 6 hours, dehydrated and paraffin embedded. Tissue blocks were cut into 4 mm sections, deparaffinized, rehydrated and treated with 3% hydrogen peroxide for 5 minutes. After blocking with 20% swine serum, sections were incubated with rabbit anti-CCKB receptor antibodies directed against the third extracellular loop of the receptor (Tarasova et al. (1994) *Letters in Peptide Science* 1: 221-228) at 1:500 dilution followed by staining with LSAB-2 kit (DAKO Corp, Carpinteria, Calif.). The slides were counter stained with Mayer's hematoxylin and observed under a Nikon Optiphot II light microscope. Original magnification: A, 8×; B,C,F, 100×; E, 400×.

Reverse Transcriptase-Polymerase Chain Reaction on Isolated Renal Tubules

Sections of kidney were digested with collagenase and microdissected to isolate individual glomeruli and tubular segments. RT-PCR (Boehringer Mannheim) was performed on 1-4 mm segments of individual tubules. Primers corresponding to unique regions of the CCKBR that spanned an exon-intron junction were used to amplify target cDNAs from the indicated nephron regions under the following conditions (denaturation at 94° C. for 45 sec; annealing at 60° C. for 25 sec; extension at 72° C. for 60 sec for a total of 28 cycles with the final extension at 72° C. for 15 min.).

Renal Tubular Physiologic Responses.

Male Wistar-Kyoto rats (300 grams, 10-12 weeks old) (Harlan Sprague Dawley, Indianapolis, Ind.) were maintained on a regular Purina rat chow diet. Catheters were placed into the external jugular and femoral veins and left carotid artery and systemic arterial pressure was monitored. The right suprarenal artery was cannulated with a PE-10 catheter heat stretched to 180 mm and a flow catheter was secured around the right renal artery (Transonic Systems, Ithaca, N.Y.). GFR was determined after an intravenous infusion of normal saline containing [$^{14}$C]-inulin (0.01 mCi/ 10 ml (New England Nuclear, Boston, Mass.) at a rate of 5 ml/100 g body wt. for 30 minutes followed by an infusion of 1.8 ml/100 g body wt/hr). After an equilibration period of 120 minutes, 20 minute collections were begun. Meal gavage studies were performed with 2.5 ml/hr of liquefied rat chow administered via gastric tube. Gastrin 17-1 (Peninsula Laboratories, CA) was diluted in normal saline and infused (10 pmoles/kg/hr) via the right renal artery catheter. Following a basal period, rats received either L-365,260 (80 pmoles/kg, 5 min bolus) or vehicle alone and 20 minute collection periods were begun for determination of sodium and water excretion.

$Na^+$-$K^+$-ATPase Activity

Renal tubules (cortical and medullary thick ascending limb of Henle) were isolated (Slobodyansky et al. (1995) *Am. J. Physiol.* 268: F279-F284) and immediately homogenized (in a Polytron) in 4° C. reaction buffer [4 mM $MgCl_2$, 100 mM tris(hydroxymethyl)aminomethane HCl, pH7.2]. The dephosphorylation of tris(hydroxymethyl)aminomethane-p-nitrophenyl-phosphate was used as the index of $Na^+$-$K^+$-ATPase activity (Eisner et al. (1997) *Am. J. Physiol.* 273: R317—R323).

Results and Discussion

To determine whether CCKB/gastrin receptors are functionally positioned to mediate the proposed regulatory action of gastrin on renal excretion, the cellular localization of CCKB/gastrin receptors within the kidney was determined by immunohistochemistry. Specific antibodies directed against the third extracellular loop of the CCKB/gastrin receptor (12) were used for staining rat, guinea pig and human kidney tissue sections. Similar to guinea pig and human, immunostaining of CCKBR expression in rat kidney was moderate in the cortex (CT), most intense in the inner stripe of the outer medulla (OMIS), less intense in the outer stripe of the outer medulla (OMOS) and absent from the inner medulla (IM). Higher magnification revealed cortical CCKBR expression in proximal tubules (PT), particularly in early segments found to be in continuity with Bowman's capsule of the glomerulus (GLOM)). A higher magnification of the junction between the inner stripe of the outer medulla (OMIS) and the inner medulla (IM) revealed the striking localization of staining limited to the inner stripe that was also present at the basolateral surface of cells within the medullary thick ascending limb (MTAL). Occasional CCKB/gastrin receptor positive cells within the glomerulus (GLOM) appeared to be either on the outer aspect of the glomerular tuft consistent with visceral epithelial cells (single arrow) or less well identified cells located deeper within the tuft (double arrow). Immunohistochemistry also localized CCKB/gastrin receptor on afferent arterioles and medium sized blood vessels within the kidney. Cortical tissue processed with pre-immune serum showed only trace staining of vascular lumina consistent with non-specific erythrocyte peroxidase activity. Overall, the relative level of CCKB/gastrin receptor expression detected by immunohistochemistry in the kidney was significantly higher than in the stomach, an organ well characterized for CCKB/gastrin receptor expression.

RT-PCR using oligonucleotide primers based upon the rat CCKB/gastrin receptor cDNA sequence amplified a product of the expected size (344 bp) (Wank et al. (1992) *Proc. Natl. Acad. Sci., USA,* 89: 8691-8695) from total RNA isolated from microdissected, isolated segments of nephrons. Consistent with their localization by immunohistochemistry, RT-PCR detected transcripts in the glomerulus, proximal tubule, and collecting duct. No PCR products were obtained from the distal convoluted tubule.

Figure 5A:
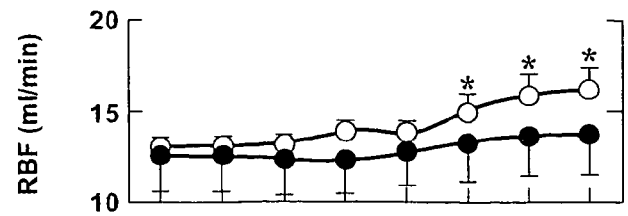
FIG. 5A through FIG. 5E show the effects of meal gavage on renal hemodynamics, sodium excretion and urine volume in rats. Following a basal interval, the rats were infused with either L-365,260 (80 pmoles/kg, 5 min bolus) (closed circles) or vehicle alone (open circles) prior to meal gavage with standard rat chow (2.5 ml/hr) and the following parameters of renal function were measured.
Figure 5B:
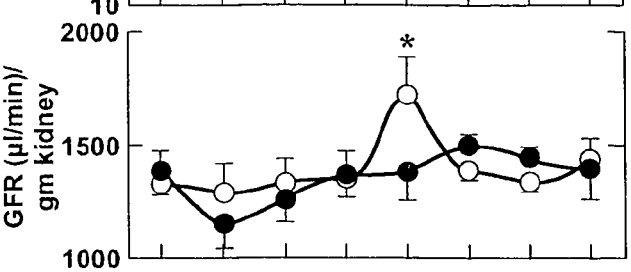
Figure 5C:
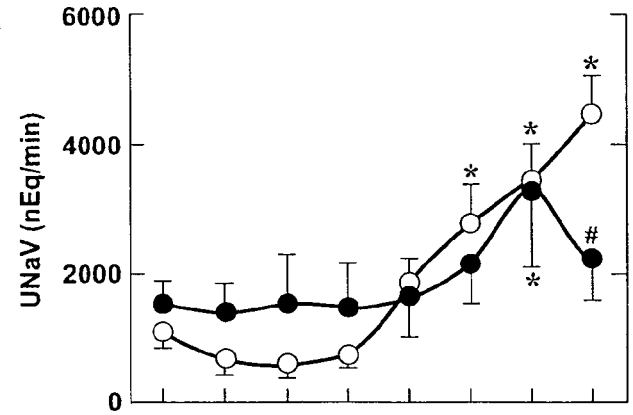
Figure 5D:
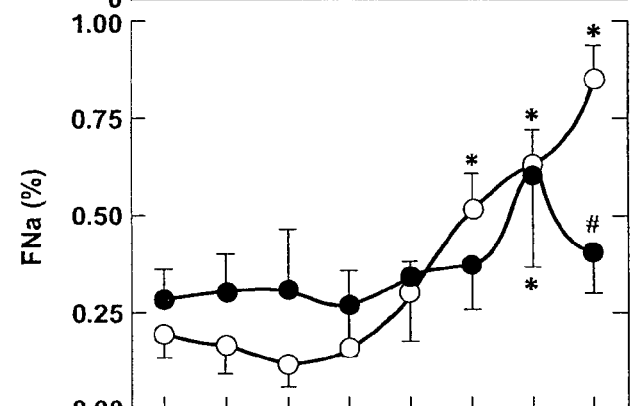
Figure 5E:
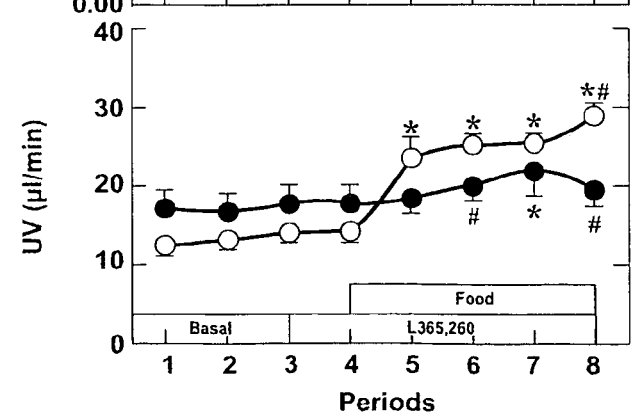

The physiologic regulation of renal function through the CCKB/gastrin receptor was investigated in male Wistar-Kyoto rats. Renal hemodynamic and tubular functions were measured following meal ingestion by gastric gavage with liquefied rat chow (previously shown to increase serum gastrin two-fold (Aurang et al. (1997) *Am. J. Physiol.* 272: G1243-G1248)) either alone or with the addition of a maximal inhibitory dose of the CCKB/gastrin receptor specific antagonist, L-365,260 (FIGS. 5A and 5B). Meal ingestion caused a small but significant increase in glomerular filtration rate (GFR) and renal blood flow (RBF) compared to basal values that was inhibited by L-365,260 administration (FIG. 3, panels a and b). In parallel with the meal stimulated elevation in serum gastrin (data not shown), urinary sodium (UNaV) and fractional excretion of sodium (FeNa=$UNa^+ \times V/GFR$ [$SNa^+$]), a measure of the renal tubular reabsorption of sodium, both increased more than 5-fold. The increases in UNaV and FeNa were both suppressed to 2-fold in the presence of L-365,260 (FIG. 5C and FIG. 5D). In parallel with the increase in sodium excretion during the meal, the urinary flow rate more than doubled (FIG. 5E). This meal-stimulated increase in urine flow rate was nearly completely inhibited in the presence of L-365,260 compared to vehicle alone (FIG. 5E). Gastric gavage with an equivalent volume and sodium concentration as the liquified rat chow (used as a negative control) had no significant effect on the above parameters of renal function during the study period (data not shown). The ability of L-365,260 to inhibit up to 80% of the meal-stimulated increase in sodium and water excretion indicates that gastrin is responsible for the majority of this effect and that other meal stimulated hormones have a minor role in sodium regulation in response to a meal. Because the proximal tubule is the major site of solute and water reabsorbtion, the most likely site of action of postprandially released gastrin is at CCKBR expressed on the proximal tubules. The observation that gastrin increases the fractional sodium excretion to a greater extent than renal blood flow also provides evidence that the site of gastrin action in the kidney is at the level of the proximal tubule.

Figure 6A:
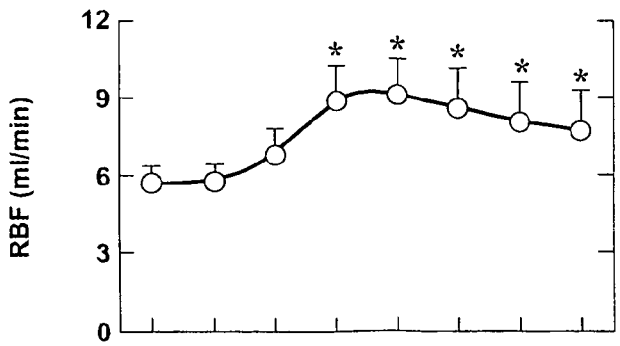
FIGS. 6A through 6E shows the effects of intrarenal administration of gastrin on renal hemodynamics, renal sodium excretion and urine volumes in rats. Gastrin (10 pmoles/kg/hr) with or without the CCKBR antagonist, L-365,260 (80 pmoles/kg, 5 min bolus) was infused via the right renal artery and the following parameters were measured.
Figure 6B:
Figure 6C:
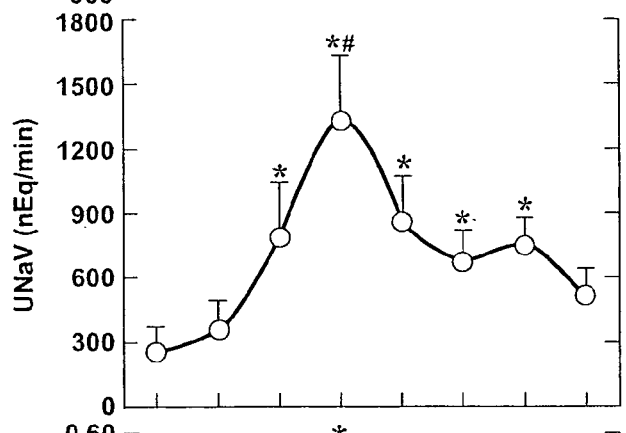
Figure 6D:
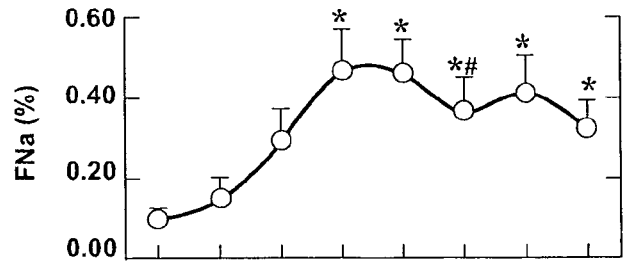
Figure 6E:
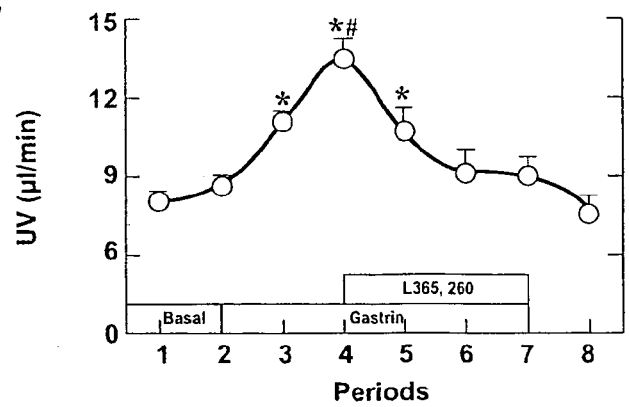

To exclude extrarenal actions of gastrin that may indirectly influence renal function, gastrin was infused directly into the right renal artery at previously determined postprandial concentrations and renal hemodynamic and tubular responses were compared to baseline and the control infusion of vehicle alone in the left renal artery. Renal hemodynamic and tubular responses to infused gastrin were determined separately for the infused right kidney compared to the non-infused left kidney. Gastrin administration caused small but significant increases in RBF (FIG. 6A) compared to basal values and GFR (FIG. 6B) in the right kidney compared to the control left kidney (FIG. 6B). This is consistent with the presence of CCKBRs identified by immunohistochemistry on renal arterioles as well as previous studies demonstrating peripheral vasodilatory effects of gastrin in rat (Guth (1991) *Scand. J. Gastroenterol.* 26 (suppl. 180): 118-125). Urinary sodium excretion (UNaV) and fractional sodium excretion (FeNa) were measured following infusion of gastrin into the right renal artery alone or with subsequent administration of L-365,260. Simultaneous urine volumes were determined by separate ureteral catheters. Urinary sodium excretion was increased more than four-fold by gastrin infusion to the right kidney compared to baseline, the recovery period and the control left kidney (FIG. 6C). Following administration of L-365,260, the gastrin-stimulated elevation in the urinary excretion of sodium returned to near baseline values indicating that the results were specific for gastrin acting at the CCKBR. The fractional sodium excretion, FeNa, increased almost fourfold compared to baseline (FIG. 6D). Similar to the results obtained for the urinary sodium excretion, following administration of L-365,260, FeNa returned to near baseline values. In parallel with the increase in sodium excretion following gastrin administration, the urinary flow rate almost doubled in the right kidney compared to the control left kidney (FIG. 6E). These changes in urine flow rate were completely antagonized by L-365,260, and unaffected by vehicle alone, again indicating the specific site of action at the CCKB/gastrin receptor. No significant change in renal function was observed in the control left kidney and the renal preparation remained stable throughout the eight period duration of the study (data not shown).

To further demonstrate the direct intrarenal action of gastrin and to determine the biochemical mechanism for gastrin's natriuretic activity, the effect of the physiological elevation of meal stimulated gastrin on $Na^+$-$K^+$-ATPase activity was measured in the proximal tubule (PT) and medullary thick ascending limb of Henle (mTAL). Following a meal, $Na^+$-$K^+$-ATPase activity was significantly inhibited in both the PT (12.79±1.37%) and mTAL (13.58±1.09%) compared to unfed control rats (FIG. 7). The complete reversal of this meal induced inhibition of $Na^+$/$K^+$-ATPase activity by direct intrarenal infusion of the CCKB/gastrin receptor specific antagonist, L-365,260, prior to the meal indicates that the CCKB/gastrin receptor mediates the full inhibitory effect of the meal. (FIG. 7). The decrease in the $Na^+$-$K^+$-ATPase activity with a meal and it's reversal by the CCKBR specific antagonist were paralleled by an increase and reversal in sodium excretion and urine flow, respectively (data not shown).

Intestinal cholecystokinin (CCK), another potent agonist at the CCKB/gastrin receptor is also released in response to a meal. However, it is unlikely to account for the effect of a meal on renal function because of the relatively low circulating level of CCK. Although the type A cholecystokinin receptor is also expressed in the kidney (15), gastrin has extremely low affinity for this receptor.

The results reported here demonstrate that CCKB/gastrin receptors are expressed at high levels within the renal tubule where they are directly stimulated by meal induced elevations in serum gastrin to increase the excretion of sodium and water absorbed during the meal. The potent inhibitory effect of gastrin on $Na^+$-$K^+$-ATPase activity demonstrated in this study is the likely intracellular mechanism responsible for the observed decrease in $Na^+$ reabsorbtion in the proximal tubule and medullary thick ascending limb of Henle. However, other cellular mechanisms such as inhibition of the $Na^+$/$H^+$ exchanger (NHE3) or increase in tubular cGMP-mediated regulation of the cystic fibrosis transmembrane conductance regulator (CFTR) as suggested for uroguanylin may also be involved (Yun et al. (1997) *Proc. Natl. Acad. Sci., USA,* 94: 3010-3015; Forte et al. (1996) *Am. J. Kid. Dis.* 28: 296-304).

While this study does not exclude other neurohormonal factors, it strongly supports gastrin as the major integrator between the gastrointestinal and renal systems following a meal. Other meal stimulated gastrointestinal hormones have been shown to affect renal function, such as glucagon and VIP, however, their effect on renal hemodynamics and tubular function occurs only at pharmacological concentration (Briffeuil et al. (1996) *J. Metabolism* 45: 383-388; Nair et al. (1994) *Diabetes Care* 17: 711-716; Lonergan and Field (1991) *Clin. Exp. Pharmacol. Physiol.* 18: 819-826). A number of non-gastrointestinal hormones and peptides that are indirectly elevated following a meal, such as prostaglandins, adrenomedulin, atrial natriuretic peptide, kinins, and substance P, affect renal tubular function indirectly (Reddy et al. (1998) *Nephron* 79: 192-200; Jougasaki et al. (1997) *Am. J. Physiol.* 272(2): F260; Long et al. (1990) *Prostaglandins* 40: 591-595; Fildes and Atkins (1997) *Am. J. Physiol.* 272(5 Pt 2):R1396-1401; Capasso et al. (1989) *Pflugers Arc.* 415: 336). Therefore, gastrin is the first meal-stimulated gastrointestinal peptide hormone shown to effect a natriuresis at physiologic levels through a direct receptor mediated action on renal tubules. Recent data for pentagastrin stimulated urinary sodium excretion in human subjects (Example 1) indicate that the findings presented in this study have important clinical implications regarding nutritional and pharmacological factors regulating the renal reabsorbtion of solutes and water and may ultimately lead to novel therapeutic strategies for improved salt and water homeostasis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing the efficacy of a gastric $H^+/K^+$-ATPase pump inhibitor (PPI) in a human in need of a PPI treatment, said method comprising:
    injecting into said human an effective amount of one or more agents selected from the group consisting of a pentagastrin and a gastrin, in conjunction with an amount of said gastric proton pump inhibitor effective to reduce gastric acid secretion, whereby the efficiency of said gastric proton pump inhibitor is increased.

2. The method of claim 1, wherein said one or more agents is pentagastrin.

3. The method of claim 2, wherein said human is a human diagnosed with a pathology characterized by excess gastric acid secretion.

4. The method of claim 3, wherein said pathology is selected from the group consisting of Zollinger/Ellison syndrome (ZES), gastroesophageal reflux disease (GERD), peptic ulcer disease, atrophic gastritis, esophagitis, and idiopathic gastric acid hypersecretion.

5. The method of claim 2, wherein said injecting comprises injecting said pentagastrin prior to administration of said gastric proton pump inhibitor.

6. The method of claim 2, wherein said injecting comprises injecting said pentagastrin simultaneously to administration of said gastric proton pump inhibitor.

7. The method of claim 2, wherein said proton pump inhibitor is selected from the group consisting of rabeprazole, omeprazole, lansoprazole, pantoprazole, and cogeners or racemic mixtures thereof.

8. The method of claim 2, wherein said injecting is subcutaneous injection.

9. The method of claim 2, wherein said pentagastrin is administered in a dosage ranging from about 0.1 mg/kg/hr to about 10 mg/kg/hr.

10. The method of claim 2, wherein said proton pump inhibitor is omeprazole.

11. A kit for the treatment of a pathology characterized by excess gastric acid secretion, said kit comprising:
    a container containing a proton pump inhibitor (PPI); and
    a container containing one or more agents selected from the group consisting of a pentagastrin and a gastrin, wherein the gastrin or pentagastrin is formulated for administration by injection.

12. The kit of claim 11, wherein said one or more agents is pentagastrin.

13. The kit of claim 12, wherein said proton pump inhibitor is selected from the group consisting of rabeprazole, omeprazole, lansoprazole, pantoprazole, and cogeners and or racemic mixtures thereof.

14. The kit of claim 12, wherein said PPI is present in a pharmaceutically acceptable excipient or diluent.

15. The kit of claim 12, wherein said PPI is dehydrated.

16. The kit of claim 12, wherein said pentagastrin is present in a pharmaceutically acceptable excipient or diluent.

17. The kit of claim 12, wherein said pentagastrin is dehydrated.

18. The kit of claim 12, further comprising an antibiotic.

19. The kit of claim 18, wherein said antibiotic is selected from the group consisting of penicillin based antibiotics, tetracyclines, macrolides, cephalosporins, and fluoroguinolones.

20. The kit of claim 12, wherein said kit further comprises instructional materials describing the use of pentagastrin in conjunction with a PPI to reduce gastric acid secretion.

* * * * *

UNITED STATES PATENT AND TRADEMARK OFFICE
CERTIFICATE OF CORRECTION

| | | |
|---|---|---|
| PATENT NO. | : 7,365,047 B1 | Page 1 of 1 |
| APPLICATION NO. | : 09/671764 | |
| DATED | : April 29, 2008 | |
| INVENTOR(S) | : Joseph R. Pisegna | |

It is certified that error appears in the above-identified patent and that said Letters Patent is hereby corrected as shown below:

SPECIFICATION:
Column 1, delete the entire paragraph at lines 16 - 19.

Signed and Sealed this
Twentieth Day of December, 2011

David J. Kappos
*Director of the United States Patent and Trademark Office*

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: pentagastrin
<220> FEATURE:
<221> NAME/KEY: MOD_RES
<222> LOCATION: (5)..(5)
<223> OTHER INFORMATION: F is modified with amide
<220> FEATURE:
<221> NAME/KEY: MOD_RES
<222> LOCATION: (1)..(1)
<223> OTHER INFORMATION: A is modified with T-boc
```

```
-continued

<400> SEQUENCE: 1

Ala Trp Met Asn Phe
1               5

<210> SEQ ID NO 2
<211> LENGTH: 4
<212> TYPE: PRT
<213> ORGANISM: Artificial Sequence
<220> FEATURE:
<223> OTHER INFORMATION: gastrin C-terminal tetrapeptide

<400> SEQUENCE: 2

Trp Met Asn Phe
1

<210> SEQ ID NO 3
<211> LENGTH: 4
<212> TYPE: PRT
<213> ORGANISM: Artificial Sequence
<220> FEATURE:
<223> OTHER INFORMATION: Blocked gastrin C-terminal tetrapeptide
<220> FEATURE:
<221> NAME/KEY: MOD_RES
<222> LOCATION: (1)..(1)
<223> OTHER INFORMATION: W is blocked with boc

<400> SEQUENCE: 3

Trp Met Asn Phe
1
```